United States Patent [19]

Kuesters et al.

[11] 4,144,156

[45] Mar. 13, 1979

[54] MANUFACTURE OF UNSYMMETRIC MONOACETALS OF AROMATIC 1,2-DIKETONES EMPLOYABLE AS PHOTOINIATIATORS

[75] Inventors: Werner Kuesters, Ludwigshafen; Manfred Jacobi, Frankenthal; Rolf Osterloh, Ludwigshafen, all of Fed. Rep. of Germany

[73] Assignee: BASF Aktiengesellschaft, Ludwigshafen, Fed. Rep. of Germany

[21] Appl. No.: 787,569

[22] Filed: Apr. 14, 1977

[30] Foreign Application Priority Data

Apr. 14, 1976 [DE] Fed. Rep. of Germany ....... 2616382
Apr. 14, 1976 [DE] Fed. Rep. of Germany ....... 2616408

[51] Int. Cl.² ............................. C08F 2/46; C08F 4/00
[52] U.S. Cl. ............................. 204/159.23; 96/115 P; 204/159.15; 204/159.16; 204/159.18; 204/159.19; 204/159.24; 260/837 R; 260/865; 260/590 D; 427/54; 428/481; 428/413
[58] Field of Search .............. 204/159.22, 159.23, 204/159.14, 159.15, 159.24, 159.16, 159.18; 260/590 D, 615 A; 96/115 P

[56] References Cited

U.S. PATENT DOCUMENTS

| | | | |
|---|---|---|---|
| 3,715,293 | 2/1973 | Sandner et al. | 204/159.14 |
| 3,998,712 | 12/1976 | Hickmann et al. | 204/159.15 |
| 4,007,209 | 2/1977 | Hickmann et al. | 204/159.23 X |
| 4,037,021 | 7/1977 | Adams | 204/159.23 X |

*Primary Examiner*—Richard B. Turer
*Attorney, Agent, or Firm*—Keil & Witherspoon

[57] ABSTRACT

Unsymmetrical monoketals of aromatic 1,2-diketones

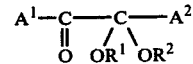

wherein $R^1$ and $R^2$ are different radicals, are manufactured by reacting the corresponding aromatic 1,2-diketones, in an organic solvent, with an acid ester $(R^1)_nX$ as alkylating agent and an alcoholate $(R^2O)_m$Me, where n and m are integers from 1 to 3, X is an acid radical and Me is a metal of main groups 1 to 3 of the periodic table of the elements. The resulting diketone monoacetals are particularly suitable for use as photoinitiators in photopolymerizable compositions.

8 Claims, No Drawings

MANUFACTURE OF UNSYMMETRIC MONOACETALS OF AROMATIC 1,2-DIKETONES EMPLOYABLE AS PHOTOINIATIATORS

The present invention relates to new unsymmetric monoacetals of aromatic 1,2-diketones, to a new process for the manufacture of new monoacetals of aromatic 1,2-diketones from the corresponding 1,2-diketones and to photopolymerizable compositions containing such compounds as photoinitiators.

The polymerization of unsaturated monomers, or of their mixtures with unsaturated polymers, by UV irradiation in the presence of photoinitiators has been disclosed. Though many photoinitiators are already known, their practical usefulness is restricted by some inherent disadvantages. For this reason, new compounds suitable for this application are of particular interest. The more recently discovered photoinitiators include compounds of the type of the benzil-monoacetals (cf. U.S. Pat. No. 3,715,293, German Laid-Open Applications DOS Nos. 2,232,365 and 2,337,813), which do not suffer from some of the disadvantages of earlier photoinitiators. The conventional process for the manufacture of compounds of this type is described by Kuhn and Trieschmann in Chemische Brichte 94 (1961), 2258 and in German Laid-Open Application DOS No. 2,337,813; according to this process, compounds of the benzil type are reacted with a dialkyl sulfite in the presence of an acid and an alcohol to give the corresponding monoacetals.

We have now found new non-cyclic unsymmetrical monoketals of aromatic 1,2-diketones which are easily manufactured and are sufficiently stable in polymerizable mixtures or compositions under conventional processing and storage conditions, but exhibit a high reactivity when the compositions are cured by irradiation, and at the same time cause exceptionally little yellowing of the compositions.

Accordingly, the present invention relates to monoketals of aromatic 1,2-diketonenes having the formula

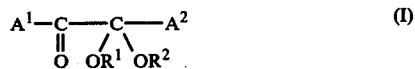

where $A^1$ and $A^2$ are identical or different aromatic radicals each of which has from 6 to 12 carbon atoms and may or may not bear from one to four hydrocarbon radicals of 1 to 10 carbon atoms, alkoxy radicals of 1 to 10 carbon atoms, alkoxyalkyl radicals of 2 to 10 carbon atoms, alkylthio radicals of 1 to 6 carbon atoms and/or halogen as substituents and $R^1$ and $R^2$ are hydrocarbon radicals of 1 to 12 carbon atoms in which the chain may or may not be interrupted by —O— or —S— or bear a halogen, which are characterized in that $R^1$ and $R^2$ represent not identical but different radicals. This type of non-cyclic unsymmetrical monoketals of aromatic 1,2-diketones has not previously been disclosed.

It is a further object of the present invention to provide a process for the manufacture of such unsymmetrical monoketals of aromatic 1,2-diketones from the corresponding 1,2-diketones, which permits simple production of the monoketals in high yields.

We have found that this object is achieved and that non-cyclic unsymmetrical monoacetals of aromatic 1,2-diketones of the formula (I) given above can be manufactured particularly advantageously from corresponding aromatic 1,2-diketones of the formula (II)

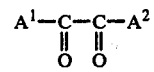

by a method wherein the 1,2-diketones of the formula (II) are reacted, in an organic solvent, with an acid ester $(R^1)_nX$ as alkylating agent and an alcoholate $(R^2O)_m Me$, where $R^1$ and $R^2$ have the above meaning, n and m are integers from 1 to 3, X is a monobasic, dibasic or tribasic acid radical and Me is a metal of the first 3 main groups (groups 1a, 2a and 3a) of the periodic table of the elements and especially a metal of atomic number from 11 to 20 from these groups of the periodic table of the elements.

It has further been found that unsymmetrical monoacetals of aromatic 1,2-diketones of the formula (I) given above can advantageously be used as the photoinitiator for curing by UV irradiation a photopolymerizable compound having at least one polymerizable carbon-carbon double bond and mixtures of such a compound.

Particularly suitable aromatic 1,2-diketones of the formula (II) are those where $A^1$ and $A^2$ are substituted benzene radicals, suitable substituents being, above all, hydrocarbon radicals of 1 to 10 carbon atoms, e.g. alkyl or phenyl, alkoxyalkyl of 2 to 10 carbon atoms, alkoxy of 1 to 10 carbon atoms, alkylthio of 1 to 6 carbon atoms or halogen.

Examples of aromatic 1,2-diketones from which the monoketals of the invention are derived are benzil and substituted benzils, e.g. 4,4'-dimethylbenzil, 4,4'-diisopropylbenzil, 4,4'-di-tert.-butylbenzil, 4,4'-diphenylbenzil, 2,2'-dimethoxybenzil, 4,4'-dimethoxybenzil, 4-methylbenzil, 3-methoxybenzil, 2,2'-dimethylbenzil, 4-chloro-4'-phenylbenzil, 4,4'-dichlorobenzil, 3,3'-dibromobenzil, 2,4,2',4'-tetramethylbenzil, 2,4,6-trimethylbenzil and 2,4-dichloro-4'-methylbenzil. The manufacture of these benzil derivatives is described in the literature; for example, they may be manufactured by oxidizing the corresponding benzoins.

Suitable alkylating agents for the manufacture of the unsymmetrical monoketals have the above formula $(R^1)_nX$ and are esters of monobasic, dibasic or tribasic acids, especially of acids containing a sulfur atom, a phosphorus atom or a halogen atom. Examples are the esters of sulfuric acid, of sulfurous acid, of phosphoric acid and of phosphorous acid, the esters of hydrohalic acid, e.g. the chlorides, bromides and iodides, and esters of the aliphatic and aromatic sulfonic acids, e.g. the mesylates, tosylates, brosylates and benzenesulfonates. The sulfates, halides and sulfonates are particularly suitable, and amongst these the sulfates and bromides are preferred. The ester radical $R^1$ is preferably a substituted or unsubstituted hydrocarbon radical of 1 to 12 carbon atoms, examples being, above all, the appropriate alkyl (especially of 1 to 6 carbon atoms), aralkyl (especially of 7 to 9 carbon atoms), alkenyl (especially of 3 to 5 carbon atoms) and aralkenyl (especially of 9 or 11 carbon atoms) radicals, and the groups Z—(CHR$^3$—CHR$^4$)p— or Z—(CHR$^3$)p—, where p is a number from 1 to 3, $R^3$ and $R^4$ are H or $CH_3$ and Z is halogen, $OR^5$, $SR^5$, OAr or SAr, where $R^5$ is alkyl of 1 to 4 carbon atoms or alkoxyalkyl of 2 to 5 carbon atoms and Ar is a six-membered aromatic radical.

Examples of alkylating agents which can be used for this process are dimethyl sulfate, diethyl sulfate, dihexyl sulfate, diallyl sulfate, dicrotyl sulfate, di-(β-phenylethyl) sulfate, di-(γ-phenylallyl) sulfate, di-(2-methoxyethyl) sulfate, di-(2-phenoxyethyl) sulfate, di- (methylthioethyl) sulfate and di-(2-phenylthioethyl) sulfate, benzyl bromide and allyl bromide.

Most of the suitable alkylating agents are known to those skilled in the art and are commercially available as such, sometimes being referred to as agents for basic or cold alkylation, or are simple to manufacture in accordance with processes disclosed in the literature.

Alcoholates, having radicals $R^2$, which do not correspond to the $R^1$ of the alkylating agent are used, i.e., for example, an ethylate, e.g. sodium ethylate or potassium ethylate, when using dimethyl sulfate as alkylating agent, or, for example, sodium methylate when using allyl bromide as alkylating agent. In other respects, the above data regarding the radicals $R^1$ apply, in a general sense, to the nature of the radicals $R^2$. Sodium and potassium alcoholates are preferred.

Examples of organic solvents or solvent mixtures which are very suitable for the present process are aromatic solvents, e.g. benzene, toluene, xylene or o-dichlorobenzene and aliphatic solvents, e.g. dioxane, tetrahydrofuran, glycol ethers, ethylene chloride, dimethylformamide and the like. Dioxane and dimethylformamide are preferred solvents. The amount of solvent should advantageously be such that after mixing all the reactants the reaction mixture can still be stirred easily. This is generally the case if the solvent accounts for at least about half the reaction mixture.

The reaction, according to the invention, of the 1,2-diketones with the alkylating agent and the alcoholate is in general carried out at from $-50°$ to $+150°$ C., preferably at from $-20°$ to $100°$ C. The reaction time depends on the particular reactants, the temperature and the batch size. In general, however, the reaction is complete within a few hours and in some cases it is complete almost as soon as the reactants have been brought together.

Theoretically, 1/n mole of alkylating agent of the above formula $(R^1)_nX$ is reacted with 1 mole of 1,2-diketone and 1/m mole of alcoholate of the above formula $(R^2O)_mMe$, with n and m in the fractions corresponding to the numbers n and m, respectively, in the formulae of the alkylating agent and alcoholate used, in order to produce the unsymmetrical monoacetals of the aromatic 1,2-diketones. In general it is however preferred to use some of the reactants in excess in order to achieve complete conversion. Thus, from 1/n to 10/n mole or more, preferably from 1/n to 4/n mole, of alkylating agent, and from 1/m to 10/m mole or more, preferably from 1/m to 4/m mole, of alcoholate can be used per mole of 1,2-diketone.

In an advantageous embodiment of the process of the present invention, the process is carried out by introducing the alcoholate into a reaction mixture consisting of the aromatic 1,2-diketone, the alkylating agent and the solvent. The alcoholate can, in such cases, be added as the solid or as a slurry, for example in dimethylformamide, dioxane or tetrahydrofuran. A further possible way of adding the alcoholate is in the form of a very concentrated solution in the alcohol on which the alcoholate is based. An example is a solution of about 20% strength of sodium methylate in methanol. However, the process can also be carried out by adding the alkylating agent as the last component to the reaction mixture.

In a further embodiment of the process of the present invention, the reactants are brought together in optional sequence in a nonpolar solvent, e.g. toluene, preferably at room temperature, and the mixture is stirred. The reaction to give the 1,2-diketone monoacetal can be accelerated by gradually adding a polar solvent, e.g. dimethylformamide or dioxane.

After the reaction has ended (which can very easily be ascertained by, for example, thin layer chromatography), it is advisable to destroy any residual dimethyl sulfate by adding bases, e.g. ethanolamine or aqueous sodium hydroxide solution, with or without heating of the reaction mixture. During the process and isolation of the reaction products, it is necessary to ensure that the reaction mixture does not assume an acid pH since otherwise hydrolysis of the monoacetal to the corresponding 1,2-diketone may occur.

The reaction mixture can be worked up, and the reaction product isolated, by conventional processes, e.g. precipitation, extraction, distillation and the like. An example of a suitable procedure is simply to add water to the reaction solution, or run the reaction solution into water. Hereupon, the desired monoacetals of the 1,2-diketones frequently separate out as a crystalline precipitate or, in some cases, as oils. A precondition for this method is, however, that the solvent used for the reaction is water-miscible.

A particularly preferred possible method of working up the reaction solution is to remove the solvent from the reaction mixture, after addition of water, by azeotropic distillation. After this distillation the water-insoluble monoacetal separates out, especially on cooling, as a crystalline substance or as an oil, often in an analytically pure or virtually analytically pure form. This method offers the advantage that the solvent employed in the reaction can be substantially recovered. Examples of unsymmetrical monoketals of aromatic 1,2-diketones according to this invention and which can be obtained by the process described are benzil methylethyl monoketal, benzil methylbenzyl monoketal, benzil methyl-crotyl monoketal, benzil methyl-allyl monoketal, 4,4'-dimethyl benzil ethyl-β-phenylethyl monoketal, 2,2'-dimethoxy benzil allyl-methyl-thioethyl monoketal, 4,4'-diphenyl benzil methyl-methoxyethyl monoketals and similar compounds manufactured from the aromatic 1,2-diketones, alkylating agents and alcoholates mentioned in this specification above.

The acetals obtained are outstandingly suitable for use as photoinitiators, especially for the photopolymerization of olefinically unsaturated monomers, and of mixtures of such monomers, by means of UV radiation. The photoinitiators are very suitable for photocuring coatings based on unsaturated polyester resins, and for the imagewise photo-crosslinking of photosensitive materials for photo resists or photopolymer printing plates.

Such photopolymerizable compositions, polymerizable by UV irradiation, and comprising (a) at least a compound with at least one polymerizable carbon-carbon double bond, or mixtures containing such compounds, and (b) monoketals of aromatic 1,2-diketones as photoinitiators advantageously contain from 0.01 to 10, and preferably from 0.05 to about 4% by weight, based on the photopolymerizable compound(s) or its or their mixtures with compatible polymeric binder(s), of the monoketals of the 1,2-diketones according to this invention.

All compounds, possessing at least one carbon-carbon double bond, which, when mixed with the photoinitiator, can be caused to undergo polymerization, may be used for such compositions. Compounds and materials possessing carbon-carbon double bonds, which are activated by, for example, aryl, carbonyl, amide, ester, carboxyl or cyanide groups, halogen atoms or other carbon-carbon double bonds, or carbon-carbon triple bonds, are very suitable. Examples include styrene, vinyltoluene, acrylic acid and methacrylic acid, and their esters, cyanides or amides, e.g. acrylamide, N-methylolacrylamide, diethers obtained from 1 mole of glycol and 2 moles of N-methylolacrylamide, methyl methacrylate, methylene-bis-acrylamide, m-phenylene-bis-acrylamide or m-xylylene-bis-acrylamide, as well as diurethanes with at least two acrylic or methacrylic groups.

To the photopolymerizable compounds, the choice of which, for each particular application of the compositions, is readily made by those skilled in the art, may be added, in the conventional way, compatible unsaturated and/or saturated polymers as binder and/or conventional additives, such as thermal polymerization inhibitors, e.g. hydroquinone or tert.-butylhydroquinone, skin-forming materials, e.g. paraffin, flow control agents, e.g. silicone oil, fillers and/or pigments or dyes, in the conventional amounts. Such mixtures are known to those skilled in the art, and the nature and amount of the additives depend in particular on the manner in which the mixtures are to be used.

The new photoinitiators have proved of particular value in unsaturated polyester resins for the manufacture of coatings curable by UV radiation. Suitable compositions based on unsaturated polyester resins comprise, for example, a mixture of (1) from 40 to 85 percent by weight of a conventional unsaturated polyester, (2) from 60 to 15 percent by weight of one or more copolymerizable olefinically unsaturated monomers and (3) from 0.5 to 5 percent by weight, based on the amount of (1) and (2) of the said monoketals of the 1,2-diketones as photoinitiator, and optionally (4) further conventional additives.

Suitable unsaturated polyesters (1) are the conventional polycondensation products of polybasic, especially dibasic, carboxylic acids, linked by ester bonds to polyhydric, especially dihydric, alcohols; these polyester binders may in addition contain radicals of monobasic carboxylic acids and/or radicals of monohydric alcohols and/or radicals of hydroxycarboxylic acids.

Suitable olefinically unsaturated monomeric compounds (2) for the unsaturated polyester resins are all conventional monomeric compounds copolymerizable with unsaturated polyesters, especially vinyl-aromatics, e.g. styrene, and esters of acrylic acid or methacrylic acid with alkanols of 1 to 8 carbon atoms, e.g. tert.-butyl acrylate or methyl methacrylate, as well as mixtures of these monomers. The preferentially used mixtures contain from 60 to 15, preferably from 50 to 25, percent by weight of component (2), the percentage being based on the sum of the amounts of components (1) and (2).

The new photoinitiators may also be used with advantage in photopolymerizable compositions which are used for the manufacture of optical information-fixing systems, especially for the manufacture of photopolymer printing plates or of photoresist coatings. For use in the manufacture of an optical information-fixing system, compositions are particularly suitable which comprise in addition to the photoinitiator, at least one monomer having at least two photopolymerizable carbon-carbon double bonds or a mixture of compounds which have at least one photopolymerizable carbon-carbon double bond which mixture contains at least 50% by weight of one or more monomers having at least two photopolymerizable carbon-carbon double bonds and a compatible polymer.

For these purposes, suitable compositions with compounds with at least one polymerizable carbon-carbon double bond are mixtures of (a) from about 10 to 60, preferably from 15 to 35, percent by weight of monomers having predominantly (as explained in the preceding sentence) at least two photopolymerizable carbon-carbon double bonds, e.g. diacrylates or dimethacrylates of aliphatic diols, bis-acrylamides and bis-methacrylamides of aliphatic or aromatic diamines of 2 to 8 carbon atoms, or monomers which in addition to at least two acrylic or methacrylic groups contain ester, amide, urethane or urea groups, with (b) from 90 to 40, preferably from 85 to 65, percent by weight of compatible polymers which are soluble in an organic solvent, e.g. an alcohol, ketone or ether. Examples of compatible polymers suitable as binders are copolyamides, e.g. those obtained from ε-caprolactam, hexamethylenediammonium adipate and p,p′-diaminodicyclohexylmethane adipate, as well as soluble polyurethanes, polyureas, butadiene or isoprene copolymers, including block copolymers, such as the polystyrene-polyisoprene-polystyrene block copolymers or cellulose derivatives soluble in organic or alkaline aqueous solvents.

Further information regarding the choice of suitable monomers and/or polymers and/or mixtures, and regarding their processing, is adequately provided, for those skilled in the art, in the published patent literature.

Particularly advantageous radiation sources for the light which initiates the photopolymerization or photocrosslinking of the mixtures are those which emit light having a wavelength of from 230 to 450 nm. Above all, radiation sources with emission maxima in the range of from 300 to 380 nm, or sources which emit a sufficiently high proportion of their light in this wavelength range, may be used. Mercury medium pressure lamps are particularly suitable, but mercury high pressure and low pressure lamps and superactinic fluorescent tubes may also be used. The said lamps may or may not be doped.

The photopolymerizable mixtures containing the new photoinitiators, may be used for the production of coatings, especially coatings based on polyester resins, inter alia for the manufacture of photopolymer printing plates, the manufacture of holograms, photoresist coatings and poromer hides, for information-fixing in general, and for UV curable printing inks. Compared to mixtures containing symmetrical benzil monoketals of the type of benzil dimethylketal, the mixtures according to the invention are distinguished by less yellowing of the cured compositions.

In the Examples which follow, parts and percentages are by weight. Parts by volume bear the same relation to parts as that of the liter to the kilogram.

EXAMPLE 1

21.6 parts of sodium methylate are added in portions in the course of 3 hours to a solution of 52.5 parts of benzil and 68.4 parts of benzyl bromide in 400 parts by volume of dimethylformamide at room temperature, whilst stirring. The reaction mixture is then stirred for 30 minutes at room temperature, after which it is stirred into 2,000 parts by volume of water. The precipitate which separates out is filtered off, washed with water and dried. It is then suspended in 150 parts by volume of petroleum ether, filtered off, washed once with petroleum ether and dried. 62.0 parts of benzil methyl-benzyl-monoketal of melting point 83°–84° C. are obtained.

EXAMPLE 2

34 parts of sodium ethylate are added in portions, in the course of one hour, to a solution of 52.5 parts of benzil and 63 parts of dimethyl sulfate in 250 parts by volume of dioxane at room temperature, whilst stirring. After adding 300 parts by volume of water and 22 parts of solid sodium hydroxide, the reaction mixture is heated under reflux for 30 minutes, 350 parts by volume of dioxane/water azeotrope are then distilled from the reaction mixture, and the residue, after cooling to room temperature, is extracted with 150 parts by volume of chloroform. 2 parts of animal charcoal are added to the chloroform extract, the extract is boiled up and filtered and the solvent is evaporated off on a rotary evaporator. The oily, substantially colorless residue, the benzil methyl-ethyl-ketal, becomes crystalline after some time. Melting point 52°–54° C.

EXAMPLE 3

48 parts of sodium methylate are added in portions, in the course of 2.5 hours, to a solution of 105 parts of benzil and 121 parts of allyl bromide in 500 parts by volume of dimethylformamide at room temperature, whilst stirring. After adding 2,000 parts by volume of water, the reaction mixture is extracted with four times 100 parts by volume of chloroform and the combined chloroform extracts are then washed with three times 200 parts by volume of water. The chloroform phase is concentrated on a rotary evaporator and the residue is then distilled under reduced pressure. 115 parts of benzil methyl-allyl-ketal, boiling at 135°–136° C./0.3 mm Hg are obtained.

EXAMPLE 4

Benzil methyl-monoketal, of boiling point 140°–145° C./0.3 mm Hg, is prepared by the method described in Example 3. Yield: 119 parts (80% of theory).

EXAMPLE 5

An unsaturated polyester is prepared by esterifying 431 parts of maleic anhydride and 325 parts of phthalic anhydride with 525 parts of 1,2-propylene glycol. After adding 0.01% of hydroquinone, a 66% strength solution of the polyester in styrene is prepared (solution A).

3 parts of photoinitiator are added to 97 parts of solution A (solution B). The shelf life (gel time) of this mixture is determined at 60° C., in the absence of light. For the photo-curing experiments, 10 parts of a 1% strength solution of paraffin (softening range 50°–52° C.) in styrene are added to 100 parts of solution B and the resin is applied, by means of a film spreader (500 μm gap width) onto hard fiberboard coated with photographic paper. After being allowed to evaporate in air for about 2 minutes, the films are exposed to fluorescent lamps (emitting a high proportion of UV light), placed at a distance of 4 cm. The rate of curing is determined by measuring the König pendulum hardness (DIN 53,157) and is summarized in Table 1 together with the color measurements obtained on the cured films.

TABLE 1

| Photoinitiator | Pendulum hardness after minutes | | | Color measurement of the films: yellowness index after exposure | Shelf life at 60° C. (hours) |
| --- | --- | --- | --- | --- | --- |
| | 4 | 8 | 10 | | |
| benzil methyl-benzyl-monoketal | 90 | 104 | 108 | 18.5 | 78 |
| benzil methyl-allyl-monoketal | 62 | 92 | 99 | 13.8 | 56–71 |
| benzil methyl-crotyl monoketal | 74 | 98 | 104 | 11.6 | not measured |
| benzil dimethyl-monoketal | 92 | 105 | 108 | 21.1 | 80–105 |

EXAMPLE 6

A reaction product of 1 mole of bisphenol-A diglycidyl ether with 2 moles of acrylic acid is dissolved in butanediol diacrylate to give a 65% strength solution. 3 percent by weight of the photoinitiators listed in Table 2 and 3 are added to this solution. 80 μm thick layers of the clear finishes are knife-coated onto white photographic paper and irradiated by means of a mercury high pressure lamp having an output of 80 watt/cm of arc length. The distance between the lamp and the surface-coating film is 10 cm. The samples are caused to travel under the UV lamp on a conveyor belt of continuously variable speed. The speed of travel of the conveyor belt (in m/min) at which scratch-resistant curing of the surface-coating films is just still attainable, is determined.

Scratch-resistant curing means that vigorously rubbing the surface of the coating with a fingernail does not break the film surface. The degree of whiteness of samples which have been cured whilst travelling at 11 m/min is also determined, by Berger's method.

TABLE 2

| Photoinitiator | Maximum curing speed (m/min) | Whiteness[x] (by Berger's method) |
| --- | --- | --- |
| benzoin n-butyl ether | 16 | 93.3 |
| p-tert.-butyl-trichloro-acetophenone | 16 | 94.0 |
| benzil dimethyl-ketal | 24 | 92.7 |
| benzil methyl-benzyl-ketal | 24 | 94.0 |

[x]higher values indicate less yellowing.

After 5 days' storage at 20° C. and 65° C., the clear finishes, mixed with photoinitiators, are retested (see Table 3).

TABLE 3

| Photoinitiator | Maximum curing speed in m/min after 5 days' storage at | |
|---|---|---|
| | 20° C | 65° C |
| benzoin n-butyl ether | 14 | prematurely polymerized |
| p-tert.-butyl-trichloro-acetophenone | 16 | no curing |
| benzil dimethyl-ketal | 24 | 24 |
| benzil methyl-benzyl-ketal | 24 | 24 |

We claim:

1. In a composition photopolymerizable with UV radiation and containing a compound having at least one polymerizable carbon-carbon double bond and further containing a photoinitiator, the improvement which comprises; using as the photoinitiator an unsymmetric monoketal of an aromatic 1,2-diketone of the formula

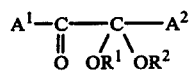 (I)

where $A^1$ and $A^2$ are identical or different aromatic radicals each of which having from 6 to 12 carbon atoms which are either unsubstituted or which may bear from one of four substituents selected from the group consisting of hydrocarbon radicals having 1 to 10 carbon atoms, alkoxy radicals having 1 to 10 carbon atoms, alkoxyalkyl radicals having 2 to 10 carbon atoms, alkylthio radicals having 1 to 6 carbon atoms and/or halogen and $R^1$ and $R^2$ are hydrocarbon radicals of 1 to 12 carbon atoms in which the chain may or may not be interrupted by —O— or —S— or bear a halogen, said radicals $R^1$ and $R^2$ being characterized in that they differ one from another.

2. A photopolymerizable composition as set forth in claim 1 wherein said photoinitiator is benzil methylethyl monoketal.

3. A photopolymerizable composition as set forth in claim 1 wherein said photoinitiator is benzil methylbenzyl monoketal.

4. A photopolymerizable composition as set forth in claim 1 wherein said photoinitiator is benzil methyl-crotyl monoketal.

5. A photopolymerizable composition as set forth in claim 1 wherein said photoinitiator is benzil methyl-allyl monoketal.

6. A photopolymerizable composition as set forth in claim 1 wherein said photoinitiator is 4,4'-dimethyl benzil ethyl-β-phenylethyl monoketal.

7. A photopolymerizable composition as set forth in claim 1 wherein said photoinitiator is 2,2'-dimethoxy benzil allyl-methylthioethyl monoketal.

8. A photopolymerizable composition as set forth in claim 1 wherein said photoinitiator is 4,4'-diphenyl benzil methyl-methoxyethyl monoketals.

* * * * *